United States Patent [19]

Szántay et al.

[11] 4,089,856
[45] May 16, 1978

[54] 1-ETHYL-1-(ALKOXYCARBONYLETHYL)-OCTAHYDRO-INDOLO[2,3-a]QUINOLIZINES

[75] Inventors: Czaba Szántay; Lajos Szabó; György Kalaus; Egon Karpáti; László Szporny, all of Budapest, Hungary

[73] Assignee: Richter Gedeon Vegyészeti Gyár Rt., Budapest, Hungary

[21] Appl. No.: 699,084

[22] Filed: Jun. 23, 1976

[30] Foreign Application Priority Data

Jun. 27, 1975 Hungary .................................. RI 570

[51] Int. Cl.$^2$ ............................................. C07D 459/00
[52] U.S. Cl. ......................... 260/293.53; 260/293.55; 260/296 P
[58] Field of Search .................. 260/293.53; 424/267, 424/256

[56] References Cited

U.S. PATENT DOCUMENTS

| 3,454,583 | 7/1969 | Kuehne | 260/293.53 |
| 3,755,333 | 8/1973 | Szantay et al. | 260/293.53 |

OTHER PUBLICATIONS

Morrison et al., "Organic Chemistry," 2nd Ed., Allyn and Bacon, Inc., Boston (1966), pp. 671 and 673.
Morrison, R. T. et al., "Organic Chemistry," Allyn and Bacon, Inc., Boston, 1959, p. 553.

Primary Examiner—Henry R. Jiles
Assistant Examiner—Richard A. Schwartz
Attorney, Agent, or Firm—Karl F. Ross

[57] ABSTRACT

Racemic and optically active 1-alkyl-1,2,3,4,6,7,12,12b-octahydro-indolo[2,3-a]quinolizines of vasodilatory and haemodynamic effect are disclosed.

5 Claims, No Drawings

1-ETHYL-1-(ALKOXYCARBONYLETHYL)-OCTAHYDRO-INDOLO[2,3-a]QUINOLIZINES

The invention relates to racemic and optically active 1-alkyl-1,2,3,4,6,7,12,12b-octahydro-indolo[2,3-a]quinolizines and the cis and trans-isomers and salts thereof. With valuable pharmaceutical activity.

It is known that 1-ethyl-1-(β-methoxy-carbonylethyl)-1,2,3,4,6,7,12,12b-octahydro-indolo[2,3-a]quinolizine is an intermediate product of vincamine synthesis (Lloydia, 27, 435 (1964), U.S.A Pat. No. 3,454,583, Belgian Pat. Spec. No. 765,006, DOS No. 2 115 718 prepared by reacting triptamine and 4-ethyl-4-formyl-dimethylpimelate and by reacting phosphorous pentasulphide with the lactam ester thus obtained and desulphurating the thiolactam ester thus formed and; thus a mixture of the cis and trans isomers is obtained.

The disadvantage of this process is that the starting materials are not easily available and the preparation thereof is complicated and so are the individual steps of the synthesis.

It has now been found that the racemic and optically active and the pure cis or trans isomers of 1-alkyl-1,2,3,4,6,7,12,12b-octahydro-indolo[2,3-a]quinolizines of the following formula

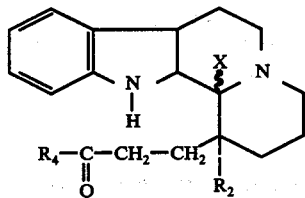

I wherein $R_1$ represents a hydroxy group or a $C_{1-18}$-alkoxy group $R_2$ stands for $C_{1-6}$ alkyl group and X stands for a hydrogen atom at cis or trans position related to the substituent $R_2$ and the salts thereof
are prepared by a simpler method which comprises reacting 1-alkyl-2,3,4,6,7,12-hexahydro-indolo[2,3-a]quinolizine of the formula II

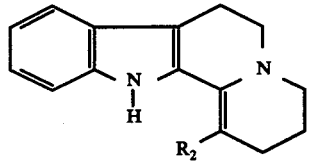

II wherein $R_2$ stands for an alkyl group containing 1 to 18 carbon atoms or an acid addition salt thereof with an acrylate of the general formula III

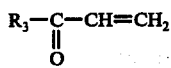

III wherein $R_3$ represents an alkoxy group—and reducing the compound of the general formula IV

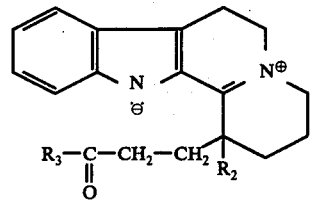

IV thus obtained
wherein $R_2$ and $R_3$ are as defined above — or an acid addition salt thereof, and, if desired, hydrolyzing the ester to give the corresponding free acid of the formula I having a hydroxy group at the position of $R_1$ and/or converting the acid into another alkyl ester of the formula I — and, if desired, converting the compound of the formula I thus obtained to an acid addition salt, to a quaternary salt or in case of free acids to a metal salt, and, if desired, resolving the intermediate or the end products of the reaction into optically active antipodes and optionally carrying out the further reaction steps with optically active compounds and/or isolating the pure cis or trans isomers from a mixture of cis and trans isomers of an intermediate product of the synthesis and optionally carrying out the further reaction steps with pure cis or trans compounds.

The reesterification of an ester of the formula I to an ester having a different alkoxy group at the position of $R_3$ is carried out either directly by a reesterification known per se or in several steps by a method also known per se (a) by hydrolysis and by esterifying the free carboxylic acid or a slat thereof—of the formula I with an alkylating agent or (b) by hydrolysis and by treating the free carboxylic acid with a halogenating agent and reacting the halide thus obtained with an aliphatic alcohol of the formula $R^1OH$.

Among the compounds of the formula I prepared by the process according to the invention only those compounds are known wherein $R_1$ is a methoxy group, $R_2$ is an ethyl group and X is a hydrogen atom at cis or trans position related to $R_2$, the other compounds are new.

If $R_1$ represents an alkoxy group, it preferably stands for a straight chain or branched alkoxy group containing 2 to 18 carbon atoms, such as ethoxy, n-propoxy, i-propoxy, prim-n-butoxy, sec.-n-butoxy, prim-i-butoxy, tert.-i-butoxy, n-pentoxy, i-pentoxy, n-hexoxy, i-hexoxy, n-heptoxy, i-heptoxy, n-octyloxy, i-octyloxy, n-nonyloxy, i-nonyloxy, n-dexyloxy, i-decyloxy, or cetyloxy. Particularly $R_1$ is methoxy, ethoxy, i-propoxy, sec.-butoxy, tert.-butoxy or n-octyloxy, and if $R_2$ is different from methyl, $R_1$ can also be methoxy.

If $R_2$ represents an alkyl group, it preferably is a $C_{1-6}$ straight chain or branched alkyl group such as methyl, ethyl, n-propyl, i-propyl, n-butyl, n-pentyl, i-pentyl, n-hexyl or i-hexyl particularly ethyl or n-butyl groups.

According to the present invention preferably such compounds of the formula I are prepared wherein $R_1$ is a hydroxy group, a methoxy group, i-propoxy group, sec. butoxy group, tert. butoxy or an n-octyloxy group, $R_2$ is an ethyl group or n-butyl group and X stands for a hydrogen atom at cis or trans position relative to $R_2$.

The compounds of the formula I—wherein $R_1$ stands for a sec. butoxy or tert.butoxy group and $R_2$ is an ethyl group and X is a hydrogen atom at the cis position relative to $R_2$—are particularly advantageous.

The starting materials of the formula II— wherein $R_2$ is as defined above—are preferably used in the form of their salts, particularly in the form of acid addition salts. An acid addition salts preferably perhalides, such as perchlorate, perbromate etc. as well as any other acid addition salts of the compound of the formula II obtained from the appropriate organic or inorganic acid can be used.

The compound of the formula II used in the form of an acid addition salt is released from its acid addition salt before the reaction in an inert organic solvent with the aid of a base. The solution is dried and the compound of the formula II thus released in an inert organic solvent can be directly used for the reaction with compounds of the formula III—wherein $R_3$ is an alkoxy group.

As a base a diluted aqueous solution of an inorganic base can be used, e.g. alkali metal hydroxides, such as sodium hydroxide, potassium hydroxide. As an inert organic solvent a solvent immiscible with water can be used, such as halogenated hydrocarbons, including chloroform, carbontetrachloride, dichloromethane, 1,2-dichloromethane, trichloroethylene preferably dichloromethane. The base is preferably released in an inert atmosphere, preferably in an atmosphere of argon or nitrogen. The process takes a relatively short time at room temperature.

The compounds of the formula III—wherein $R_3$ stands for an alkoxy group—and optionally an inert organic solvent such as tert. butanol are added to a solution prepared with an inert organic solvent described above, of the compounds of the formula II—wherein $R_2$ is an alkyl group.

Reaction time and temperature of the reaction of the compounds of the formulae II and III are not of special importance, but the reaction is preferably carried out at room temperature and within 6 hours to 6 days. If desired, inert atmosphere such as an atmosphere of argon or nitrogen can be used. Compounds of the formula IV—wherein $R_2$ is an alkyl group and $R_3$ an alkoxy group —are obtained in the form of an inner salt, but the compound obtained can be treated with an acid to form an acid addition salt. Such acids are for example inorganic acids such as hydrohalides, preferably hydrochloric acid, perhalogen acids, preferably perchloric acid, etc.

Compounds of the formula IV—wherein $R_2$ is alkyl and $R_3$ is alkoxy —are subjected to reduction either in the form of an inner or of an acid addition salt. The reduction can be conducted by any method which is suitable for saturating the double bond of the ring. The reduction is preferably conducted with a chemical reducing agent or with catalytically activated hydrogen.

When conducting the reduction with a chemical reducing agent, the latter is preferably a complex metal hydride; particularly borohydrides such as lithium borohydride, potassium borohydride or sodium borohydride are used. The reduction is preferably conducted with a chemical reducing agent or with catalytically activated hydrogen. When conducting the reduction with a chemical reducing agent, as a reducing agent preferably a complex metal hydride, particularly borohydrides such as lithium borohydride, potassium borohydride or sodium borohydride are used.

The reduction carried out with borohydride is conducted in an inert solvent or suspending agent and preferably an aliphatic alcohol such as methanol, aqueous alcohol such as aqueous methanol is used.

The borohydride is added to the reaction mixture in excess, preferably in an about 1.5 to 7 fold molar amount. The temperature of the reaction and the reaction time are not important from the point of view of the reduction, the factors mentioned above are dependent in the first place upon the reactivity of the starting materials used. The reaction is usually conducted at a temperature of about 0° C and after mixing the reactants the mixture is further stirred for a time ranging from 15 minutes to 3 hours.

According to an advantageous embodiment of the present invention a compound of the formula IV—wherein $R_2$ and $R_3$ are as defined above —are suspended in an inert solvent, preferably in an aliphatic alcohol, the suspension is cooled to about 0° C and the borohydride, preferably sodium borohydride, is added at this temperature in small portions. The reaction is worked up by known techniques such as by decomposing the reaction mixture by acidifying or by concentration of the mixture, by dissolving the residue in water, by alkalizing the residue or by extracting it with an inert solvent or by evaporating the extract. When conducting the reduction by catalytically activated hydrogen metals such as palladium, platinum, nickel, iron, copper, cobalt, chromium, zinc, molybdenum, tungsten or the oxides or sulfides thereof etc. are used as the catalyst.

The catalysts can be prepared for example by reducing the stable oxides thereof with hydrogen directly in the reaction vessel. This procedure can be applied when using highly dispersed platinum or palladium as a catalyst. Catalysts prepared from a biner alloy by acidic or alkaline extraction, such as Raney nickel can also be used. The catalytical hydrogenation can be carried out in the presence of such catalysts which had been precipitated on the surface of a carrier; thus a much smaller amount of the expensive noble catalyst is necessary to carry out the reduction. Such carriers are for example coal, particularly charcoal, silicon dioxide, aluminum oxide, sulfates and carbonates of the alkali earth metals.

Among the catalysts palladium, particularly palladium on charcoal or Raney-nickel are preferred, but the selection of the catalysts is always dependent upon the properties of the substance to be hydrogenated and on the reaction conditions.

The catalytical hydrogenation can be conducted in an inert solvent such as alcohols, ethyl acetate, glacial acetic acid etc. or the mixture of these solvents. As a solvent preferably aliphatic alcohols, such as methanol, or ethanol are used. When using palladium on charcoal catalyst preferably an acidic or neutral medium is used; when using Raney-nickel catalyst preferably a neutral or alkaline medium is used.

The temperature, the pressure and the reaction time of the catalytical hydrogenation of the invention can vary over a wide range according to the starting compounds, but the reaction is preferably conducted at room temperature and under atmospheric pressure until the hydrogen consumption is finished. The hydrogen consumption lasts for about 10 minutes to 5 hours.

The reaction mixture is worked up by known methods for example by filtering the reaction mixture after the hydrogen consumption had stopped and the filtrate is evaporated to dryness.

According to an advantageous embodiment of the reduction conducted with catalytically activated hydrogen, the catalyst washed with water and with a solvent used during the hydrogenation, preferably with methanol such as palladium on charcoal is first prehydrogenated whereafter a solution of the compound of the formula IV or a salt thereof in the solvent mentioned above is added and the hydrogenation is conducted preferably at room temperature, under atmospheric pressure until the hydrogen consumption comes to an end. When working up the reaction mixture the product is usually obtained in a crystalline form.

However, when the product is obtained in the form of an amorphous dust or of an oil, the product can easily be crystallized with the conventional organic solvents such as methanol, ethanol, iso-propanol, aliphatic ethers such as diethyl ether etc. An isomeric mixture of the compounds of the formula I —wherein $R_1$ is identical with $R_3$, $R_2$ is an alkyl group and X is a hydrogen atom at trans or cis position related to $R_2$—is separated after optional resolution by a conventional physical method such as by fractionated crystallization for example in an organic solvent preferably in a lower aliphatic carboxylic acid ester or in a halogenated hydrocarbon, in a lower aliphatic ether, alcohol, particularly in methanol, ethanol or isopropanol or in the mixture of the solvents mentioned above.

The separation of the 2 isomers can also be carried out on the base of different physical properties, particularly on the base of different $R_f$ values by applying layer chromatography, caused by the fact that the $R_f$ value of the trans isomer is higher, than that of the cis isomer. As an adsorbent silica gel (Merck $PF_{254-366}$) is used and as an eluating system different solvent combinations can be used such as benzene-methanol, preferably 14:2 (Halpaap, H.: Chemie-Ing.Techn. 35, 488 1963).

According to a further feature of the present invention the separation of the two isomers can be conducted by hydrolysin the cis and trans isomer mixture of the formula I—obtained after the reduction and optionally resolved—wherein $R_1$ is identical with $R_3$, $R_2$ is an alkyl group and X stands for a hydrogen atom at cis or trans position related to $R_2$—followed by subjecting the isomer mixture of the carboxylic acid of the general formula I—wherein $R_1$ is hydroxy-to fractionated crystallization.

The fractionated crystallization can be carried out by dissolving the heated racemic or optically active cis and trans carboxylic acid isomer mixture in a suitable inert solvent such as dimethylformamide, and on cooling the trans isomer of lower melting point is precipitated from the solution, and on addition of water to the filtrate the cis carboxylic acid of higher melting point is also precipitated in the organic solvent.

The free carboxylic acids can also be separated into optically active antipodes, as the free carboxylic groups form readily diastereomer salts with optically active bases.

The hydrolysis giving a compound of the formula I—wherein $R_1$ is a hydroxy group, $R_2$ is an alkyl group and X is a hydrogen atom at cis or trans position related to $R_2$—is carried out by methods known per se for example in the presence of an inorganic base preferably alkali metal hydroxide such as sodium hydroxide in a solvent preferably in an aliphatic alcohol such as ethanol, preferably at the boiling temperature of the base used.

The racemic or optically active cis and trans carboxylic acids separated as described above are separately converted into an ester by a known method. The esterification can be conducted by converting the appropriate racemic or optically active cis or trans carboxylic acid of the formula I—wherein the substituents are as defined above—with a suitable halogenating agent to the appropriate carboxylic acid halide and reacting the racemic or optically active cis or trans carboxylic acid halide of the formula I —with an appropriate aliphatic alcohol and thus any desired racemic or optically active cis or trans carboxylic acid ester of the formula I — wherein the substituents are as defined above —can be prepared.

A further aspect of the present invention is the preparation of new racemic or optically active cis or trans carboxylic acids or carboxylic acid halides —wherein $R_1$ is a hydroxy group or halogen, $R_2$ is an alkyl group and X is a hydrogen atom at cis and/or position related to $R_2$.

The optically active or racemic cis or trans carboxylic acid halides can be prepared by reacting the appropriate racemic or optically active cis or trans carboxylic acid of the formula I —wherein $R_1$ is a hydroxy group, $R_2$ is an alkyl group and X is a hydrogen atom at cis or trans position related to $R_2$—with a halogenating agent by a method known per se. As a halogenating agent preferably chlorinating agents, such as thionyl chloride, phosphoroxy chloride, phosphorus thiochloride, phosphorus pentachloride, particularly thionyl chloride are used. The halogenation can be carried out in an inert solvent, but without any solvent as well. The halogenation can be conducted in the presence of an organic or inorganic base too, but the reaction can be carried out without any base as well.

The halogenation can preferably be performed at a lower temperature, preferably at about 0° C. The reaction time is not too important from the point of view of the reaction; it is preferably from 20 minutes to 2 hours. The racemic or optically active cis or trans carboxylic acid halides can be used for the next reaction step without further purification in the form of a crude product. The acid halide obtained can be reacted in the reaction mixture without separation from the reaction mixture.

The racemic or optically active cis or trans carboxylic acid halides are reacted with an aliphatic alcohol preferably at about 0° C, for 30 minutes to 2 hours.

A racemic or optically active cis or trans carboxylic acid of the formula I —wherein $R_1$ is a hydroxy group, $R_2$ and X as defined above —can also be esterified by treating the corresponding acid or a salt thereof, optionally in the presence of a base, with an alkylating agent. As salts of a carboxylic acid of the formula I preferably alkali metal salts such as sodium and potassium salts etc. can be used. As alkylating agents preferably an alkyl halide, preferably alkyl bromide, particularly alkyl iodide is used. The alkyl group of the alkyl halides is preferably a straight chain or branched $C_{1-6}$ group, such as a primary or a secondary alkyl group such as methyl, ethyl, n-propyl, i-propyl, n-butyl, sec-butyl, n-pentyl, i-pentyl, n-hexyl, or i-hexyl.

As alkylating agents for example methyl iodide, methyl bromide, ethyl iodide, ethyl bromide, i-propyl iodide, i-propyl bromide, sec. butyl iodide, sec. butyl bromide are preferred. The alkylation can be carried out in a dipolar aprotic solvent such as hexamethylphosphoric acid amide or dimethylformamide. When using a carboxylic acid of the formula I—wherein $R_1$ is a hydroxy group and $R_2$ and X are as defined above—as a starting compound, the reaction is preferably carried out in the presence of an inorganic base such as potassium hydroxide, an aqueous solution of sodium hydride, sodium hydroxide or potassium carbonate, particularly potassium carbonate. The alkylation can be carried out by forming a salt with any of the bases mentioned above, and this salt is reacted with the alkylating agent but the carboxylic acid can also be reacted with the suitable alkylating agent in the presence of a base. The products of any of the steps of the process according to the present invention and in the reaction mixture are worked up by methods known per se depending on the starting materials, the product, the solvent etc. for example when the reaction is finished the product is precipitated, separated by filtration and the product remaining in the solution is evaporated to dryness in vacuo. The dry residue is crystallized with a suitable inert organic solvent such as petroleum ether. The solvent is dependent on the solubility and crystallization of the substance to be crystallized. When working up the reaction mixture the product can be extracted with a suitable inert organic solvent such as dichloromethane, dichloroethane etc. the organic solution is dried, evaporated and the residue is, if desired, crystallized. The desired product can be precipitated from the reaction mixture with an inert organic solvent such as ether and the precipitated substance is separated by filtration.

The racemic or optically active cis or trans compounds of the formula I can be subjected, if desired, to further purification e.g. recrystallization. Suitable solvents for the recrystallization are for example aliphatic alcohols, such as methanol, ethanol, isopropyl alcohol, aliphalic ethers, such as diethyl ether etc.

The compounds according to the invention can also be purified by preparative layer chromatography. As an adsorbent silica-gel, Merck $PF_{254-366}$ is used and as a developing system different solvent mixtures such as benzene and methanol, preferably 14:2 or 14:3 and as an eluent aliphatic ethers such as diethyl ether, aliphatic ketones such as acetone can be used.

The racemic or optically active cis or trans compounds of the general formula I—wherein the substituents are as defined above—are if desired, converted to a pharmaceutically acceptable acid addition salt with an acid such as inorganic acids such as hydrogen halides, e.g. hydrochloric acid, hydrogen bromide, sulfuric acid, phosphoric acid, organic carboxylic acids, e.g. formic acid, acetic acid, propionic acid, oxalic acid, glycol acid, maleinamic acid, fumaric acid, succinic acid, tartaric acid, ascorbic acid, citric acid, malic acid, salicylic acid, lactic acid, benzoic acid, cinnamic acid, alkyl sulfonic acids, such as methane sulfonic acid, aryl sulfonic acid such as p-toluene sulfonic acid, cyclohexyl sulfonic acids, asparagine acid, glutamic acid, N-acetyl asparagic acid, N-acetyl-glutamic acid etc.

The salt formation is preferably carried out in an inert organic solvent such as aliphatic alcohols such as methanol, by dissolving the base of the formula I and by adding a suitable acid until the pH of the mixture becomes slightly acid (about pH = 6). The precipitated compound of the formula I or a salt thereof is separated from the reaction mixture with an organic solvent in miscible with water such as diethylether.

If the racemic or optically active cis or trans compounds of the formula I—wherein the substituents are as defined above—are obtained in the form of acid addition salts, the compounds of the formula I are released from the salt with a base in a suitable solvent by a method known per se. The salt is dissolved in a suitable solvent or solvents such as the mixture of acetone and water and a base such as concentrated aqueous ammonium hydroxide solution is added to this solution in an appropriate amount.

The free carboxylic acids of the formula I ($R^1 = OH$) can be converted to metal salts such as alkali metal, such as sodium, potassium or to earth metal alkali salts by methods known per se.

Compounds of the present invention of the formula I—wherein the substituents are as defined above—contain an asymmetric carbon atom. A further aspect of the present invention is the separation of the optically active antipodes. The solution of the compounds is carried out by known techniques. The resolution can be conducted as the last step of the process according to the invention but the intermediate products, e.g. the corresponding carboxylic acids can also be resolved, and the further steps are then carried out with optically active compounds. The compounds of the formula I can be, if desired, racemized.

The compounds of the formula I are prepared according to the invention with a good yield and in a form in which the compounds can be well identified and the results of the elementary analysis are near to the calculated values and the structure of the compounds of the formula I is proved by the results of the IR spectra and by the values of the magnetic nuclear resonance spectra too.

On the basis of pharmaceutical investigations the compounds of the present invention possess a considerable haemodynamic activity which can be observed in the field of vasodilatation, in blood pressure decrease and in the change of the pulse rate.

Dogs narcotized with pentobarbital were investigated. The blood circulation of the limb was measured in the femoral artery, the blood circulation of the brain was measured in the internal carotid artery, the cardiovascular resistance values were calculated from the corresponding values of the blood pressure and the blood stream.

The substances were administered intravenously in a dose of 1 mg./kg. of body weight. The average values of 6 animals related to the condition before the administration are given in the following Table.

Table 1

| Substance | The mean values of changes caused by an intravenous dose of 1 mg./kg. | | | | | |
|---|---|---|---|---|---|---|
| | 1 | 2 | 3 | 4 | 5 | 6 |
| A | +24 | −2.4 | +31 | −0.9 | −50 | +57 |
| B | +53 | −2.8 | +4 | −3.5 | −81 | +38 |
| C | +47 | −1.1 | +48 | −0.5 | −52 | +66 |
| D | +28 | −2.3 | +2 | −1.9 | −37 | +12 |
| E | +4 | −0.4 | 0 | 0 | 0 | −2 |
| F | +22 | −1.9 | +24 | −0.8 | −20 | +6 |
| G | +48 | −3.7 | +18 | −1.6 | −31 | +21 |
| H | +48 | −2.2 | +45 | −1.4 | −21 | +45 |
| I | +60 | −3.1 | +17 | −1.1 | −29 | +16 |
| J | +45 | −1.9 | +40 | −1.2 | −21 | +23 |
| K | +6 | −2.1 | +1 | −0.5 | −1 | 0 |
| L | +3 | −2.1 | +5 | −0.6 | −12 | 0 |
| Vincamin | +19 | −1.5 | +0.9 | −0.4 | −19 | −17 |

The first column in Table 1 indicates the blood stream of the limbs (ml./min.), the second column contains the cardiovascular resistance of the limbs (mmHg./ml./min.), in the third column the brain-circulation in ml./min. in. the fourth column cardiovascular resistance of the brain (mmHg./ml./min.), in the fifth column the blood pressure mmHg.) and in the sixth column the pulse rate (l./min.) values are given.

Substance A: A mixture of 1α-ethyl-1-(methoxycarbonyl-ethyl)-1,2,3,4,6,7,12,12bα-octahydro-indolo/2,3-a/quinolizine and of 1α-ethyl-1-(methoxycarbonyl-ethyl)-1,2,3,4,6,7,12,12bβ-octahydro-indolo[2,3-a]quinolizine isomers.

Substance B: 1α-ethyl-1-(methoxycarbonyl-ethyl)-1,2,3,4,6,7,12,12bα-octahydro-indolo[2,3-a]quinolizine Substance C: 1α-ethyl-1-(methoxycarbonyl-ethyl)-1,2,3,4,6,7,12,12bβ-octahydro-indolo[2,3a]quinolizine Substance D: 1α-ethyl-1-(ethoxycarbonyl-ethyl)-1,2,3,4,6,7,12,12bα-octahydro-indolo[2,3-a]quinolizine Substance E: 1α-ethyl-1-(hydroxycarbonyl-ethyl)-1,2,3,4,6,7,12,12bα-octahydro-indolo[2,3-a]quinolizine Substance F: 1α-ethyl-1-(isopropoxycrbonyl-ethyl)-1,2,3,4,6,7,12,12bα-octahydro-indolo[2,3-a]quinolizine Substance G: 1α-ethyl-1-(isopropoxycarbonyl-ethyl)-1,2,3,4,6,7,12,12bβ-octahydro-indolo[2,3-a]quinolizine Substance H: 1α-ethyl-1-(sec-butoxycarbonyl-ethyl)-1,2,3,4,6,7,12,12bα-octahydro-indolo[2,3-a]quinolizine Substance I: 1α-ethyl-1-(sec-butoxycarbonyl-ethyl)-1,2,3,4,6,7,12,12bβ-octahydro-indolo[2,3-a]quinolizine Substance J: 1α-ethyl-1-(tert-butoxycarbonyl-ethyl)-1,2,3,4,6,7,12,12bα-octahydro-indolo[2,3-a]quinolizine Substance K: 1α-ethyl-1-(n-octyloxycarbonyl-ethyl)-1,2,3,4,6,7,12,12bβ-octahydro-indolo[2,3-a]quinolizine Substance L: 1α-ethyl-1-(n-octyloxycarbonyl-ethyl)-1,2,3,4,6,7,12,12bα-octahydro-indolo[2,3-a]quinolizine It is evident from the values given in Table 1, that cis and trans isomers display a different effect in every case. Trans isomers generally display a stronger activity on the limb circulation and cis isomers are more effective in stimulating the brain circulation if $R_1$ stands for a propyloxy or butyloxy group. If the alkyl chain is shorter for example $R_1$ is a methoxy or ethoxy group the trans configuration is more effective.

According to the results the majority of the new substances show a better vasodilatating effect than Vincamine.

Especially those compounds are valuable, wherein $R_1$ is a butoxy group.

The effective dose of the compounds can vary in the range of some tenths of mg. to 1 mg. per kg. of body weight when administering the substance parenterally or orally. The dosage is determined on the basis of the needs of the patients and the experience of the physicians always accordingly to the present requirements. The doses given above are non-limiting. One or several racemic or optically active cis or trans compounds of the formula I—wherein $R_1$, $R_2$ and X are as defined above—as active ingredient(s) can be converted by admixing them with pharmaceutically acceptable nontoxic, inert solid or liquid carriers and/or excipients suitable for parenteral or enteral administration to pharmaceutical compositions. As carriers water, gelatine, lactose, milk sugar, starch, pectine, magnesium stearate, talcum, vegetable oils such as peanut oil, olive oil, gum acacia, polyalkylene glycols, vaseline can be used. The active ingredient is contained in the usual forms of pharmaceutical compositions such as solid tablets or lozenges, dragees, capsules, such as hard gelatine capsules, pellets, suppositories, etc. or liquid oily or aqueous solutions, suspensions, emulsions, syrups, soft gelatine capsules, injectable oily or aqueous solutions or suspensions etc. The amount of the solid carrier can vary in a wide range, preferably from 25 mg. to 1 g. If desired, the pharmaceutical products also contain the usual pharmaceutical excipients such as preservatives, stabilizers, wetting agents, emulgating agents, salts for adjusting the osmotic pressure, buffers, flavoring agents, ordorants, etc.

The compositions can optionally contain further pharmaceutically valuable compounds. The compositions are preferably in dosage units suitable for the desired administration method. The pharmaceutical compositions are prepared by the conventional methods which comprises screening, stirring, granulation, pressing or dissolving. The products are further subjected to the usual pharmaceutical procedures (such as sterilization).

The invention is further illustrated with the following nonlimiting Examples.

EXAMPLE 1

Inner salt of 1-ethyl-1-(methoxycarbonyl-ethyl)-1,2,3,4,6,7-hexahydro-12H-indolo[2,3-a]quinolizine 1.00 g. (2.7 mmoles) of 1-ethyl-1,2,3,4,6,7-hexahydro-12H-indolo[2,3-a]quinolizine perchlorate is suspended in 10 ml. of dichloromethane and a mixture of 2 ml. of 2 n sodium hydroxide and 7.5 ml. of water is added under constant stirring. The reaction mixture is stirred for 5-10 minutes, the organic phase is separated and dried over anhydrous potassium carbonate. 1.2 ml. of methyl acrylate are added to the anhydrous solution and the reaction mixture is stored for one night at room temperature. The next day the reaction mixture is evaporated to dryness, the residue is triturated with 8 ml. of petroleum ether. After drying 0.88 g. of inner salt of 1-ethyl-1-(methoxycarbonyl-ethyl)-1,2,3,4,6,7-hexahydro-12H-indolo [2,3-a]quinolizine are obtained in the form of orange red crystals.

Yield: 91%

M.p.: 110° C

The crude product is recrystallized from methanol, m.p.: 114°-115° C.

Elementary analysis: for the formula $C_{21}H_{26}N_2O_2 \cdot H_2O$ (molecular weight: 356.45): Calculated %: C = 70.76; H = 7.92; N = 7.86; Found %: C = 70.58, H = 7.88; N = 6.59.

IR spectrum (KBr): $\nu_{max}$: 1728 (ester =CO) cm$^{-1}$, 1603 (=C=N) cm$^{-1}$.

Magnetic nuclear resonance spectrum: (in deuterochloroform):

$\tau$ = 2.3 – 3.5 (m, 5H aromatic H);

$\tau$ = 6.44 (s, 3H, —OCH$_3$);

$\tau$ = 9.17 (t, 3H, —CH$_3$).

UV spectrum (methanol):

$\lambda_{max}$: 242 nm, log = 4.0086; 253 nm, log = 3.9813; 361 nm, log = 4.3443.

EXAMPLE 2

1-Ethyl-1-(methoxycarbonyl-ethyl)-1,2,3,4,6,7,12,12b-octahydro-indolo[2,3-a]quinolizine 300 mg. of inner salt of the 1-ethyl-1-(methoxycarbonyl-ethyl)-1,2,3,4,6,7-hexahydro-12H-indolo[2,3-a]quinolizine are dissolved in 30 ml. of methanol and 200 mg. of sodium borohydride are added under stirring steadily at 0° C. The mixture is stirred for 45 minutes. The excess sodium borohydride is decomposed with glacial acetic acid and the methanol is evaporated in vacuo. The residue is dissolved in 30 ml. of water, the pH is adjusted to 8 by adding of 5% sodium carbonate, and extracted with dichloromethane. The dichloromethane solution is dried over anhydrous magnesium sulfate and the solvent is removed by distillation in vacuo. Thus 0.27 g. of light oily product are obtained, which product is further worked up by preparative layer chromatography. As an adsorbent silica gel, Merck $PF_{254-366}$, as a developing system a mixture of benzene and methanol 14:2 is used. The substances can be eluated with ether.

The ethereal solutions are evaporated where 0.072 g. of the trans-isomer of higher $R_f$ are obtained. The physical constants of the trans isomer are as follows:

M.p.: 150°–152° C

IR spectrum (KBr): max. 1710 (ester $=CO$).$cm^{-1}$

Analysis for $C_{21}H_{28}N_2O_2$ (molecular weight: 340.34):
 calculated %: C = 74.58; H = 8.29; N = 8.23;
 found %: trans isomer C = 74.18; H = 8.37; N = 8.16; cis isomer C = 74.17; H = 8.43; N = 8.26.

IR spectrum (KBr):
 trans isomer: 3320 $cm^{-1}$ (indol —NH—), 1708 $cm^{-1}$ ($=C=O$);
 cis isomer: 3400 $cm^{-1}$ (indole —NH—), 1732 $cm^{-1}$ ($=C=O$).

Magnetic nuclear resonance spectrum: (in deuterchloroform)
 trans isomer: $\tau$ 1.15 (1H, indole —NH—), $\tau$ 2.42–2.95 (4H aromatic hydrogens); $\tau$ 6.23 (3H, $CH_3O$—), $\tau$ 9.33 (3H, alkyl —$CH_3$); cis isomer: $\tau$ 2.21 (1H, indole —NH—), $\tau$ 2.46–3.07 (4H, aromatic hydrogens, $\tau$ 6.48 (3H, $CH_3O$—), $\tau$ 8.85 (3H, alkyl —$CH_3$).

EXAMPLE 3

1-Ethyl-1-(methoxycarbonyl-ethyl)-1,2,3,4,6,7,12,12b-octahydro-indolo [2,3-a]quinolizine An isomer mixture of a ratio described in Example 2 is obtained when dissolving 147 g. of 1-ethyl-(methoxycarbonylethyl)-(methoxycarbonylethyl)-1,2,3,4,6,7-hexahydro-12H-indolo[2,3-a]quinolizine in 16 ml. of methanol and hydrogenating in the presence of 100 mg. palladium on charcoal catalyst.

The calculated amount of hydrogen is consumed by the unsaturated compound in 20 minutes.

A product of identical physical properties and yield is obtained as according to Example 2.

EXAMPLE 4

1-Ethyl-1-(sec-butoxycarbonyl-ethyl)-1,2,3,4,6,7-hexahydro-12H-indolo [2,3-a]quinolizinium perchlorate To a base prepared from 3.00 g (8.5 mmoles) of 1-ethyl-1,2,3,4,6,7-hexahydro-12H-indolo[2,3-a]quinolizine perchlorate according to Example 1 and dissolved in 40 ml. of dichloromethane 1 ml. of tert. butanol and 3 ml. of sec. butyl-acrylate are added. The reaction mixture is stored for 5 days at room temperature in the atmosphere of argon. The solvent is evaporated in vacuo and the residue is dissolved in 20 ml. of ether, acidified with perchloric acid to pH 6 and the ether is decanted from the separating oil. The residue is crystallized from 20 ml. of iso-propanol.

Yield: 3.4 g. (83%) of the title compound.

M.p.: 148°–150° C

IR spectrum (KRr): 3250 (—NH—) 1710 (ester $=CO$), 1620, 1530 $cm^{-1}$ ($=C=N$).

EXAMPLE 5

1-Ethyl-1-(sec-butoxycarbonyl-ethyl)-1,2,3,4,6,7,12,12b-octahydro-indolo[2,3a]quinolizine and the cis and trans isomers thereof 1.00 g. (2.1 mmoles) of 1-ethyl-1-(sec-butoxycarbonyl-ethyl)-1,2,3,4,6,7-hexahydro-12H-indolo[2,3-a]quinolizinium perchlorate are hydrogenated in 30 ml. of methanol in the presence of 1.0 g. of charcoal catalyst. The hydrogenation is finished in about 20 minutes. The catalyst is removed by filtration, the methanol is distilled off in vacuo, the residue is treated with 5% sodium carbonate solution and extracted with dichloromethane. The dichloromethane extract is dried over magnesium sulfate, the dichloromethane is distilled off and the residual oil is crystallized from 10 ml. of ether. The cis isomer of the precipitated title compound is filtered and washed with ether.

The weight of the product is 0.25 g.

M.p.: 142°–144° C after recrystallization from isopropanol.

IR spectrum (KBr): 3360 (—NH—), 2720, 2760 (Bohlmann bands), 1710 $cm^{-1}$ (ester CO).

The ethereal mother liquor is evaporated and thus 0.35 g. of cis-trans mixture of the title compound are prepared, and the product is purified by means of preparative layer chromatography. (KG-$PF_{254+366}$, a mixture of benzene: methanol 14:3, eluating with acetone, the $R_f$ value of the trans isomer is higher than that of the cis isomer. Thus further 0.18 g. (total yield 0.43 g. 54%) of cis isomer and 0.10 g. (12.6% of trans isomer are isolated, the latter melts at 99°–101° C (after recrystallization from isopropanol).

IR spectrum (KBr): 3300 (—NH—) 2760, 2700 (Bohlmann bands), 1698 $cm^{-1}$ (ester $=CO$).

EXAMPLE 6

1-Ethyl-1-(tert-butoxycarbonyl-ethyl)-1,2,3,4,6,7,12,12b-octahydro-indolo [2,3-a]quinolizine and the cis and trans isomers thereof From 3.00 g. (8.5 mmoles) of 1-ethyl-1-(sec-butoxycarbonyl-ethyl)-1,2,3,4,6,7-hexahydro-12H-indolo[2,3-a]quinolizinium perchlorate the base is prepared according to the method described in Example 1 and is dissolved in 40 ml. of dichloromethane. 1 ml. of tert, butanol and 3 ml. of tert-butyl-acrylate are given to the solution. The reaction mixture is stored for 4 days in the atmosphere of argon. The solvent is distilled off in vacuo and the residue is dissolved in 20 ml. of isopropanol and the pH is adjusted to 6 with 70% perchloric acid. The precipitated crystals are filtered.

Yield: 2.7 g. (66.5%) of the title compound

M.p.: 194°–195° C after recrystallization from isopropanol

IR spectrum (KBr): 3360 (—NH—), 1710 (ester $=CO$), 1618, 1525 $cm^{-1}$ ($=C=N$).

EXAMPLE 7

1-Ethyl-1-(tert-butoxycarbonyl-ethyl)-1,2,3,4,6,7,12,12b-octahydro-indolo [2,3-a]quinolizine and the cis and trans isomers thereof 2.00 g. (4.2 mmoles) of 1-ethyl-1-(tert.-butoxycarbonyl-ethyl)-1,2,3,4,6,7-hexahydro-12H-indolo[2,3-a]quinolizine perchlorate were hydrogenated in 80 ml. of methanol in the presence of 3.0 g. palladium on charcoal catalyst. After the consumption of the calculated amount of hydrogen (cca. 1 hour) the catalyst is filtered from the mixture and the methanol is distilled in vacuo from the filtrate. The residue is treated with a 5% sodium carbonate solution and is extracted with dichloromethane. The extract is dried over magnesium sulfate, the solvent is distilled off and the oil obtained is crystallized from 10 ml. of isopropanol, the precipitated cis isomer of the title compound is filtered.

Yield: 1.0 g.

M.p.: 190°–191° C

IR spectrum (KBr): 3380 (—NH—) 2780, 2720 (Bohlmann bands) 1708 cm$^{-1}$ (ester =CO)

The mother liquor is worked up by preparative layer chromatography (KG-PF$_{254+366}$, a mixture of benzene-methanol 14:3, elution with acetone), the R$_f$ value of the trans isomer is higher than that of the cis isomer, thus 0.03 g. (total yield 1.03 g., 65%) of cis isomer and 0.1 g. (6.3%) of trans isomer are separated, the latter melts at 121°–122° C (after recrystallization from isopropanol).

IR spectrum (KBr): 3320 (—NH—), 2780, 2720 (Bohlmann bands), 1695 cm$^{-1}$ (ester =CO).

EXAMPLE 8

1α-Ethyl-1-(hydroxycarbonyl-ethyl)-1,2,3,4,6,7,12,12α-octahydro-indolo [2,3-a]quinolizine and 1o-ethyl-1-(hydroxycarbonyl-ethyl)-1,2,3,4,6,7,12,12bβ-octahydro-indolo[2,3-a]quinolizine and a mixture thereof 6.00 g. of cis, trans mixture of 1-ethyl-1-(methoxycarbonyl-ethyl)-1,2,3,4,6,7,12,12b-octahydro-indolo[2,3-a]quinolizine prepared according to Example 2 are heated in 30 ml. of 95% ethanol in the presence of 1.5 g. of solid sodium hydroxide for 1 hour. The solvent is distilled off in vacuo, the residue is dissolved in 30 ml. of water and the pH of the solution is adjusted to 6 with an aqueous acetic acid solution. The precipitated product is filtered and washed with water and methanol.

Yield: 5.4 g. (93%) of an isomer mixture of the title compound.

8.00 g. of the acid mixture mentioned above are dissolved hot in 54 ml. of dimethylformamide and on cooling 3.8 g. (47.5%) of pure trans carboxylic acid are precipitated.

M.p.: 148°–150° C.

12 ml. of water are added to the mother liquor and thus 2.8 (35%) of pure cis carboxylic acid are obtained.

M.p.: 148°–150° C

EXAMPLE 9

1α-Ethyl-1-(sec-butoxycarbonyl-ethyl)-1,2,3,4,6,7,12,12bβ-octahydro-indolo [2,3-a]quinolizine (trans isomer)

(a) To 2.00 g. (3 mmoles) of 1α-ethyl-1-(hydroxycarbonylethyl)-1,2,3,4,6,7,12,12b-octahydro-indolo[2,3-a]quinolizine 4 ml. of thionyl chloride are added under cooling with ice and the mixture is stirred for 30 minutes at 0° C. The excess thionyl chloride is removed by washing with ether and by repeated decantation and 5 ml. of sec-butanol are added to the residual acid chloride.

IR spectrum (KBr): 1780 cm$^{-1}$ (acid chloride =CO) and the mixture is stirred for 1 hour at 0° C.

The obtained hydrochloric acid salt of the ester is precipitated with absolute ether and is purified by repeated decantation. After crystallization the crystals are filtered, washed with ether. The hydrochloric salt thus obtained is dissolved in water, the solution is alkalized with concentrated aqueous ammonium hydroxide solution, and extracted with dichloromethane. The extract is dried over magnesium sulfate and the organic solvent is distilled and the oil obtained is crystallized from isopropanol, thus 1.00 g. (42%) of the named compound melting at 98°–99° C are obtained, the physical properties of which are identical with those of the compound prepared in Example 5.

(b) 1.63 g. (5 mmoles) of 1α-ethyl-1-carboxyethyl-1,2,3,4,6,7,12,12bβ-octahydro-indolo[2,3-a]quinolizine are dissolved under mild heating in 12.5 ml. of hexamethylphosphoric acid amide (HMPA) and 0.80 g. of anhydrous potassium carbonate and 3.24 g. (22.3 mmoles) of sec-butylbromide are added to the solution. The reaction mixture is stirred at room temperature for 24 hours. The mixture is poured on 100 ml. of water and repeatedly extracted with ether. The combined ethereal phase is washed with water dried over magnesium sulfate. The solvent is distilled and the residual 1.60 g. of substance is crystallized from 5 ml. of isopropanol.

Yield: 1.30 g. (68.5%) of title compound.

M.p.: identical with that of the product obtained in Example a).

EXAMPLE 10

1α-Ethyl-1-(isopropoxycarbonyl-ethyl)-1,2,3,4,6,7,12,12bα-octahydro-indolo [2,3-a]quinolizine 3.00 g. (0.92 mmoles) of 1α-1-ethyl-(hydroxycarbonylethyl)-1,2,3,4,6,7,12,12b-octahydro-indolo[2,3-a]quinolizine prepared according to Example 8 are converted to acid chloride with thionyl chloride and 20 ml. of isopropyl chloride are added to the acid chloride under cooling and stirring. The reaction mixture is mixed for 1 hour at 0° C. The hydrochloric acid is precipitating which process is promoted by addition of a small amount of absolute ether. The salt thus obtained is dissolved in the mixture of concentrated acetone : water = 1:3. The solution is alkalized with an aqueous ammonium hydroxide solution, the precipitated product is filtered and washed with water.

Yield: 1.7 g. (53%) of the title compound.

M.p.: 163°–165° C (after recrystallization from isopropanol)

IR spectrum (KBr): 3400 (—NH—), 1720 cm$^{-1}$ (—CO$_2$iPr).

EXAMPLE 11

1α-Ethyl-1-(isopropoxycarbonyl-ethyl)-1,2,3,4,6,7,12,12bβ-octahydro-indolo [2,3a]quinolizine 3.00 g. (0.92 mmoles) of 1α-ethyl-1-(hydroxycarbonylethyl)-1,2,3,4,6,7,12,12bβ-octahydro-indolo[2,3-a]quinolizine is converted to an acid chloride according to the method described in Example 10. 20 ml. of isopropanol are added to the acid chloride and the mixture is stored for 1 hour at 0° C. The hydrochloric acid salt is precipitated with absolute ether, is filtered and washed with ether and dissolved in the mixture of acetone : water = 1:3 and extracted with dichloromethane. The extract is alkalized with concentrated aqueous ammonium hydroxide solution, dried over magnesium sulfate, the solvent is distilled off and the oil obtained as a residue is crystallized from isopropanol.

Yield: 1.4 g. (45%) of the title compound are obtained.

M.p.: 96°–98° C.

IR spectrum (KBr): 3320 (—NH—), 2800, 2750 (Bohlmann bands), 1710 cm$^{-1}$ (—CO$_2$iPr).

EXAMPLE 12
1α-Ethyl-1-(n-octyloxycarbonyl-ethyl)-1,2,3,4,6,7,12,12bβ-octahydro-indolo [2,3-]quinolizine To 4.0 ml. of thionyl chloride cooled to 0° C 2.0 g. (0.61 mmoles) of 1α-ethyl-1-(hydroxycarbonyl-ethyl)-1,2,3,4,6,7,12,12bβ-octahydro-indolo[2,3-a]quinolizine prepared according to Example 8 are added. After the addition the mixture is stirred for a hour. The excess thionyl chloride is removed by repeated washing with absolute ether and by decantation.

Ir spectrum (KBr): 1780 cm$^{-1}$ (acid chloride =CO). 5 ml. of n-octyl alcohol are added to the acid chloride and the reaction mixture is stirred for 1 hour at 0° C. The octyl ester hydrochloric acid salt is precipitated with absolute ether, purified by repeated decantation with ether. The mixture is worked up according to Example 11 and is purified by means of preparative layer chromatography (KG.PF$_{254+366}$, benzene : ethanol = 14:3, eluation with ether). After eluating the substance of the highest R$_f$ 1.2 g. (44%) of oily product are obtained, which is pure title compound.

IR spectrum (KBr): 3320 [—NH—], 2720, 2690 (Bohlmann bands), 1710 cm$^{-1}$ (ester = CO).

EXAMPLE 13
1α-Ethyl-1-(n-octyloxycarbonyl-ethyl)-1,2,3,4,6,7,12,12bα-octahydro-indolo [2,3-a]quinolizine The product is obtained by the process described in Example 12 using a starting material: 2 g. of 1α-ethyl-1-(hydroxycarbonyl-ethyl)-1,2,3,4,6,7,12,12bα-octahydro-indolo [2,3-a]quinolizine.

Yield: 1.32 g. (49%) of chromatographically homogeneous, oily title compound is obtained.

IR spectrum (KBr): 3350 (—NH—), 2720 (Bohlmann bands), 1720 cm$^{-1}$ (ester =CO).

EXAMPLE 14
1-n-Butyl-1-(methoxycarbonyl-ethyl)-1,2,3,4,6,7-hexahydro-12H-indolo[2,3-a]quinolizinium perchlorate 5.0 g. (13.3 mmoles) of 1-n-butyl-1,2,3,4,6,7-12H-indolo[2,3-a]quinolizinium perchlorate are suspended in 50 ml. of dichloromethane and 10 ml. of 2n sodium hydroxide solution and 40 ml. of distilled water are added to the suspension under stirring in the atmosphere of argon.

The stirring is finished after 10 to 15 minutes and the separating organic phase is isolated and dried over magnesium sulfate.

The dried substance is filtered and to the solution containing 1-n-butyl-1,2,3,4,6,7-hexahydro-indolo[2,3-a]quinolizine 5.0 ml. (55.3 mmoles) of freshly distilled methylacrylate are added. The solution turns red very quickly and the solution is saturated with argon and stored at room temperature.

After two days the starting material can not be detected even by chromatography. The solution is evaporated in vacuo. The temperature of the bath is not higher than 50° C. The residual red oil is dissolved in methanol and acidified with 70% aqueous perchloric acid to pH = 5. The mixture is stored at room temperature and 5.05 g. of yellow crystalline salt is precipitated.

The salt is recrystallized from methanol and thus 4.60 g. (74.2%) of the title compound are obtained.

M.p.: 184°–185° C.

Analysis for the formula $C_{23}H_{31}N_2ClO_6$: Calculated %: C = 59.15; H = 6.94; N = 6.00; Found %: C = 59.15; H = 6.85; N = 6.42.

IR spectrum (KBr): max. 330 cm$^{-1}$ (ind —NH), 1728 cm$^{-1}$ (=C=O), 1625 cm$^{-1}$ (=C=N=).

EXAMPLE 15
1α-n-Butyl-1-(methoxycarbonyl-ethyl)-1,2,3,4,6,7,12,12bα-octahydro-indolo [2,3-a]quinolizine (cis isomer) and
1α-butyl-1-(methoxycarbonyl-ethyl)-1,2,3,4,6,7,12,121,2,3,4,6,7,12bβ-octahydro-indolo [2,3-a]quinolizine (trans isomer)

2.60 g. (5.57 mmoles) of 1-n-butyl-1-(methoxycarbonyl-ethyl)-1,2,3,4,6,7-hexahydro-12H-indolo[2,3-a]quinolizinium perchlorate are dissolved in 100 ml. of methanol and the solution is cooled to 0° C and 1.30 g. (34.3 mmoles) of sodium borohydride are added to the solution in small proportions under stirring. The mixture is stirred for an hour after the addition whereafter the solution is acidified with 5 n hydrochloric acid solution to pH = 3. The suspension is evaporated to a volume of 15 ml. in vacuo and the evaporation residue is diluted with 200 ml. of distilled water and extracted with 50 ml. of dichloromethane.

The organic part is dried over magnesium sulfate and evaporated. The residual oil is crystallized from methanol and thus 1.45 g. (70.7%) of isomer mixture are obtained.

The isomer mixture is dissolved in methanol and 70% aqueous perchloric acid solution is added to the solution to pH = 5 and thus 1.55 g. of the title compound are precipitated.

The individual isomers are separated by fractionated crystallization from methanol.

Yield: 0.90 g. (higher R$_f$ value) of trans isomer.

M.p.: 213°–234° C.

Analysis for the formula $C_{23}H_{33}N_2ClO_4$ (molecular weight: 436.96): Calculated %: C = 63.21; H = 7.61; N = 6.41; Found %: C = 63.17; H = 7.58; N = 6.86.

IR spectrum (KBr): max. 3390 cm$^{-1}$ (ind —NH), 1738 cm$^{-1}$ (=C=O)

and 0.25 g. (lower R$_f$) of cis isomer.

M.p.: 206°–208° C

Analysis for the formula $C_{23}H_{33}N_2ClO_4$ (molecular weight: 436.96): Calculated %: C = 63.21; H = 7.61; N = 6.41; Found %: C = 63.02; H = 7.47; N = 6.70.

IR spectrum (KBr): max. 3385 cm$^{-1}$ (ind —NH), 1730 cm$^{-1}$ (=C=O).

EXAMPLE 16
Inner salt of 1-Ethyl-1-(ethoxycarbonyl-ethyl)-1,2,3,4,6,7-hexahydro-indolo[2,3-a]quinolizine 10 g. (28.4 mmoles) of 1-ethyl-1,2,3,4,6,7-hexahydro-12H-indolo[2,3-a]quinolizinium perchlorate are suspended in 100 ml. of dichloromethane and 75 ml. of distilled water and 20 ml. of 2 n sodium hydroxide solution are added to the suspension. The mixture is shaken out for 10 minutes in a separating funnel and separated. The aqueous part is shaken out with another 20 ml. of dichloromethane, the organic phases are combined and dried over magnesium sulfate.

The dried substance is filtered and 10 ml of freshly distilled ethyl acrylate are added to the filtrate. The mixture is stirred and nitrogen is passed through the mixture to drive the air and the mixture is stored covered at room temperature for 2 days. The solvent is removed by distillation in vacuo and the residual dark, oily substance is crystallized from ethanol.

Yield: 8.3 g. (79.1%) of orange crystalline product.
M.p.: 90°–92° C

Analysis for the formula $C_{22}H_{30}N_2O_3$ (molecular weight: 370.48): Calculated %: C = 71.32; H = 8.16; N = 7.56; Found %: C = 71.57; H = 8.18; N = 7.18.

IR spectrum (KBr): 1728 cm$^{-1}$ (=C=O), 1610 cm$^{-1}$ (=O=N=).

Magnetic nuclear resistance spectrum (in deuterochloroform):
$\tau$ = 2.28 (1H, ind -NH),
$\tau$ = 2.68 (4H, aromatic hydrogens),
$\tau$ = 5.95 (2H, ester —CH$_2$—),
$\tau$ = 9.20 (3H, alkyl —CH$_3$—).

EXAMPLE 17

1α-Ethyl-1-(ethoxycarbonyl-ethyl)-1,2,3,4,6, 7,12,12bα-octahydro-indolo[2,3-a]quinolizine (cis isomer) and
1α-ethyl-1-(ethoxycarbonyl-ethyl)-1,2,3,4,6,7,12,12bβ-indolo[2,3-a]quinolizine (trans isomer)

7.20 g. (19.5 mmoles) of 1-ethyl-1-(ethoxycarbonyl-ethyl)-1,2,3,4,6,7-hexahydro-indolo[2,3-a]quinolizine inner salt are suspended in 200 ml. of methanol whereafter the suspension is cooled to 0° C and in small portions 2.50 g. (66.2 mmoles) of sodium borohydride are added. After the addition the solution is stirred for a further 1 hour at 0° C and acidified with 5 n hydrochloric acid solution to pH:3 and the solution is evaporated in vacuo. The residue is suspended in water and the suspension is alkalized under cooling with 40% aqueous sodium hydroxide solution to pH=10. The mixture is extracted with 50, 30 and 20 ml. of dichloroethane and the organic phase is dried over magnesium sulfate. The dried and filtered solution is evaporated in vacuo and the residual oily part is triturated with ethanol.

Yield: 5.10 g. (74.2%) of white crystalline isomer mixture of the title compounds are obtained.

The isomer mixture is subjected to fractinated crystallization from ethanol in tenfold amount, thus 3.20 g. (46.4%) of trans isomer of the named compound, melting at 130°–132° C and 0.90 g. (13.1%) of cis isomer of the title compound, melting at 114°–115° C are obtained.

Analysis for the formula $C_{22}H_{30}N_2O_2$ (molecular weight: 354.48): Calculated %: C = 74.54; H = 8.53; N = 7.90; Found %: Trans isomer: C = 74.76; H = 8.80; N = 7.84; cis isomer: C = 74.80; H = 8.58; N = 8.12.

IR spectrum (KBr):
trans isomer: 3380 cm$^{-1}$ (indole —NH—), 1725 cm$^{-1}$ (=C=O);
cis isomer: 3430 cm$^-$(indole —NH—), 1738 cm$^{-1}$ (=C=O).

Magnetic nuclear resonance: (in deuterochloroform):
cis isomer:
$\tau$ > 2.15 (1H, indole —NH—),
$\tau$ = 2.45–300 (4H, aromatic hydrogens),
$\tau$ = 5.86 (2H, ester —CH$_2$—),
$\tau$ = 09.35 (3H, alkyl —CH$_3$);
trans isomer:
$\tau$ = 1.12 (1H, indole —NH—),
$\tau$ = 2.40–3.05 (4H, aromatic hydrogens),
$\tau$ = 5.78 (2H, ester —CH$_2$—),
$\tau$ = 9.32 (3H, alkyl —CH$_3$).

What we claim is:
1. 1α-Ethyl-1-(sec-butoxycarbonyl-ethyl)-1,2,3,4,6,7,12, 12bα-octahydro-indolo[2,3-a]quinolizine.
2. 1α-Ethyl-1-(sec-butoxycarbonyl-ethyl)-1,2,3,4,6,7,12, 12bβ-octahydro-indolo[2,3-a]quinolizine.
3. 1α-Ethyl-1-(tert-butoxycarbonyl-ethyl)-1,2,3,4,6,7,12, 12bα-octahydro-indolo[2,3-a]quinolizine.
4. 1α-Ethyl-1-(isopropoxycarbonyl-ethyl)-1,2,3,4,6,7,12, 12bα-octahydro-indolo[2,3-a]quinolizine.
5. 1α-Ethyl-1-(isopropoxycarbonyl-ethyl)-1,2,3,4,6,7,12, 12bβ-octahydro-indolo[2,3-a]quinolizine.

* * * * *